US012723225B2

(12) United States Patent
Zhang

(10) Patent No.: US 12,723,225 B2

(45) Date of Patent: Sep. 1, 2026

(54) SINGLE-CELL SCREENING DEVICE, SCREENING ASSEMBLY, SCREENING METHOD, AND USE THEREOF

(71) Applicant: Shanghai Aurefluidics Technology Co., Ltd, Shanghai (CN)

(72) Inventor: Hua Zhang, Shanghai (CN)

(73) Assignee: Shanghai Aurefluidics Technology Co., Ltd, Shanghai (CN)

( * ) Notice: Subject to any disclaimer, the term of this patent is extended or adjusted under 35 U.S.C. 154(b) by 1191 days.

(21) Appl. No.: 17/764,996

(22) PCT Filed: Oct. 21, 2019

(86) PCT No.: PCT/CN2019/112223
§ 371 (c)(1),
(2) Date: Nov. 21, 2022

(87) PCT Pub. No.: WO2021/062890
PCT Pub. Date: Apr. 8, 2021

(65) Prior Publication Data

US 2023/0242855 A1 Aug. 3, 2023

(30) Foreign Application Priority Data

Sep. 30, 2019 (CN) ......................... 201910947260.2

(51) Int. Cl.
*C12M 3/06* (2006.01)
*C12M 1/00* (2006.01)
*C12M 1/12* (2006.01)

(52) U.S. Cl.
CPC ............ *C12M 23/16* (2013.01); *C12M 25/06* (2013.01); *C12M 29/06* (2013.01); *C12M 31/06* (2013.01)

(58) Field of Classification Search
None
See application file for complete search history.

(56) References Cited

U.S. PATENT DOCUMENTS

2005/0084981 A1* 4/2005 Ostrowski ............ B01J 19/0046 436/180
2006/0223185 A1* 10/2006 Fedorov ................. C12N 13/00 435/461

FOREIGN PATENT DOCUMENTS

CN 1426845 A 7/2003
CN 1769049 A 5/2006
CN 1796127 A 7/2006
CN 101796186 A 8/2010

(Continued)

*Primary Examiner* — William H. Beisner
(74) *Attorney, Agent, or Firm* — IPRTOP LLC

(57) ABSTRACT

A single-cell screening device, a screening assembly, a screening method, and use thereof. The single-cell screening device includes a body, a plurality of spray holes, heating portions, and a flow channel. The spray holes are located in the body, the heating portions are located in the spray holes and used for heating a liquid entering the spray holes to generate bubbles so as to spray out cells. The flow channel is located in the body and extends to the spray holes according to a preset path, so as to deliver a cell suspension into the spray holes. The single-cell screening device of the present disclosure has a simple design and is easy to fabricate. Cell printing (spraying) using the screening assembly of the present disclosure has a much higher cell printing speed than conventional methods, allowing for a rapid cell sorting process.

15 Claims, 5 Drawing Sheets

(56) References Cited

FOREIGN PATENT DOCUMENTS

| | | | | | |
|---|---|---|---|---|---|
| CN | 107446820 | A | | 12/2017 | |
| CN | 108330065 | A | * | 7/2018 | ............ C12M 47/04 |
| CN | 109554332 | A | | 4/2019 | |
| EP | 2577254 | B1 | | 2/2015 | |
| KR | 20060006346 | A | * | 1/2006 | .......... B41J 2/14112 |

* cited by examiner

SINGLE-CELL SCREENING DEVICE, SCREENING ASSEMBLY, SCREENING METHOD, AND USE THEREOF

CROSS REFERENCES TO RELATED APPLICATIONS

This is a Sect. 371 National Stage application of a PCT International Application No. PCT/CN2019/112223, filed on Oct. 21, 2019, which claims priority of a Chinese Patent Applications No. 2019109472602, filed on Sep. 30, 2019, the content of which is hereby incorporated by reference in its entirety for all purposes.

TECHNICAL FIELD

The present disclosure belongs to the field of biological medicine, and relates to a single-cell screening device, screening assembly and screening method.

BACKGROUND

Methods traditionally used for single-cell screening and isolation include a microfluidic method and a limiting concentration dilution method. The microfluidic method includes collecting passing-through single cells that have been trapped by microfluidics and isolated into a single droplet, or capturing single cells by grasping them with tiny structures within a flow channel. The limiting concentration dilution method involves dispersing a cell suspension into a container such as a well plate after multiple dilutions, so that the concentration is as low as less than a single cell per well. As a result, some wells can have exactly a single cell per well. However, the production process and use of these single-cell screening and isolation methods are mostly performed manually, and they are complicated to operate, and have the disadvantages of being time-consuming, low throughput and low efficiency. Further, the limiting concentration dilution method has the disadvantage of high void fraction, and has obvious limitations and obstacles in applications such as drug screening and monoclonal antibody production.

Therefore, it has become an important technical problem for those skilled in the art to provide a single-cell screening device with simpler design and easier fabrication, and to use it for rapid screening of single cells.

SUMMARY

The present disclosure provides a single-cell screening device, a screening assembly, a screening method, and use thereof for solving the problem that the production process and use of the traditional single-cell screening and isolation methods are mostly performed manually, and are complicated, time-consuming, low-throughput and inefficient, and that the limiting concentration dilution method has the disadvantage of high void fraction.

The present disclosure provides a single-cell screening device, which includes:

- a body, including a first surface and a second surface arranged opposite to the first surface;
- a plurality of spray holes, disposed in the body, wherein the spray holes extend from openings on the second surface and extend toward the first surface without penetrating the first surface;
- heating portions, disposed in the spray holes and connected to top surfaces of the spray holes, the heating portions being used to heat liquid entering the spray holes to produce bubbles that will eject cells entering the spray holes; and
- a flow channel, disposed in the body, the flow channel extending from an opening on the first surface and extending to the spray holes in a predetermined path, to deliver a cell suspension into the spray holes.

Optionally, the flow channel includes a main flow channel and a plurality of sub-flow channels connected to the main flow channel, each of the spray holes being connected to one of the sub-flow channels.

Optionally, the plurality of sub-flow channels are distributed on two opposite sides of the main flow channel.

Optionally, the main flow channel includes a column array for lining up cells before the cell suspension enters the sub-flow channels.

Optionally, the shortest distance between each column of the column array and a corresponding sub-flow channel closest to the column is less than twice the diameter of the single cell to be screened.

Optionally, the spray holes have a diameter less than twice the diameter of the single cell to be screened.

The present disclosure further provides a single-cell screening assembly, including any of the above-mentioned single-cell screening devices. The single-cell screening assembly further includes:

- a reservoir, used for storing a cell suspension; the reservoir is provided with a liquid outlet for outputting the cell suspension to the flow channel of the single-cell screening device;
- a cell harvester, located below the single-cell screening device, for receiving target single cells ejected from the spray holes;
- a waste liquid collector, located below the single-cell screening device, for receiving non-target cells and liquid ejected from the spray holes; and
- an optical system, located below the single-cell screening device, for identifying locations and serial numbers of the spray holes containing the target single cells.

Optionally, the optical system includes a bright field light source system for identifying the number and size of the cells.

Optionally, the bright field light source system includes a microscope lens, a coaxial light path, a bright field light source, a condenser lens barrel, and a charge-coupled-device (CCD) camera, which are sequentially arranged according to a predetermined path.

Optionally, the optical system includes a fluorescent light source system for identifying cells with specific antibody labeling.

Optionally, the fluorescent light source system includes a microscope lens, a coaxial light path, a fluorescence filter, a fluorescent light source, a condenser lens barrel, and a CCD camera, which are sequentially arranged according to a predetermined path.

Optionally, the cell harvester includes a multi-well plate, each well in the multi-well plate being used to receive a target single cell.

The present disclosure further provides a single-cell screening method, which uses any of the above-mentioned single-cell screening assemblies for single-cell screening. The single-cell screening method includes the operations of:

- supplying, via the reservoir, a cell suspension to the single-cell screening device;
- identifying, via the optical system, locations of the spray holes containing the target single cells in the single-cell screening device;

moving the cell harvester to a predetermined position below the single-cell screening device, and driving, via a control circuit, the heating portions in the spray holes containing the target single cells, to sequentially eject single cells from the corresponding spray holes into the cell harvester; and moving the waste fluid collector to a predetermined position below the single-cell screening device, and driving, via a control circuit, the heating portions in the spray holes containing the non-target cells, to eject the contents in the corresponding spray holes into the waste fluid collector.

Optionally, the contents in all the spray holes containing non-target cells are simultaneously ejected into the waste liquid collector.

Optionally, the cell harvester and the waste fluid collector are simultaneously moved below the single-cell screening device, and the waste fluid collector is located below the cell harvester. When all target single cells have been ejected, the cell harvester will be removed and the waste liquid collector will be raised to the previous position of the cell harvester.

Optionally, the cell harvester and the waste liquid collector are moved by means of mechanical arms.

The present disclosure further provides a use of a single-cell screening device, including using any of the above-mentioned single-cell screening devices to eject cells, to create recoverable pores on surfaces of cell membranes, and using the pores for cell chromosome transfection.

As described above, the single-cell screening device of the present disclosure has a simple design and is easy to fabricate. Cell printing (spraying) using the screening assembly including the single-cell screening device has a much higher cell printing speed than conventional methods, allowing for a rapid cell sorting process. The camera of the microscope of the optical system scans all samples in sequence and uses images to quickly identify locations of the target cells. The target cells can be sequentially released when the non-target cells are released, thus greatly reducing the time of screening and sorting. The cell screening device of the present disclosure prints cells with minimal damage to the cells. The cell screening device of the present disclosure may have other applications, for example, the recoverable pores created on the surfaces of cell membranes during cell printing may be used as an application tool for cell chromosome transfection.

DESCRIPTION OF REFERENCE NUMERALS

Figure 1:
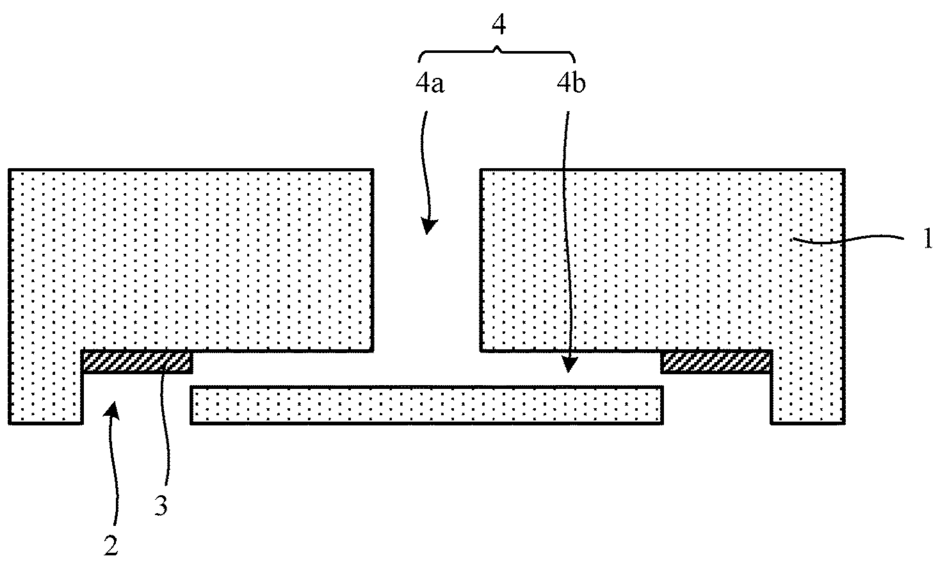
FIG. 1 shows a structural schematic diagram of the single-cell screening device of the present disclosure in a first section from a first surface toward a second surface.

1 Body
2 Spray holes
2*a* First spray hole
2*b* Second spray hole
3 Heating portion
4 Flow channel
4*a* Main flow channel
4*b* Sub-flow channel
4*b*-1 First sub-flow channel
4*b*-2 Second sub-flow channel
5 Cell
6 Column
d Distance
7 Reservoir
8 Cell suspension
9 Cell harvester
10 Waste liquid collector
11 Optical system
12*a*~12*b* Mechanical arm
13 Well
14 Bubble
15 Waste liquid collection tank

Detailed Description of The Present Disclosure

The embodiments of the present disclosure will be described below through exemplary embodiments. Those skilled in the art can easily understand other advantages and effects of the present disclosure according to the contents disclosed by the specification. The present disclosure can also be implemented or applied through other different exemplary embodiments. Various modifications or changes can also be made to all details in the specification based on different points of view and applications without departing from the spirit of the present disclosure.

Please refer to FIGS. 1-11. It needs to be stated that the drawings provided in the following embodiments are just used for schematically describing the basic concept of the present disclosure, thus only illustrating components only related to the present disclosure and are not drawn according to the numbers, shapes and sizes of components during actual implementation, the configuration, number and scale of each component during the actual implementation thereof may be freely changed, and the component layout configuration thereof may be more complex.

Embodiment 1

Figure 2:
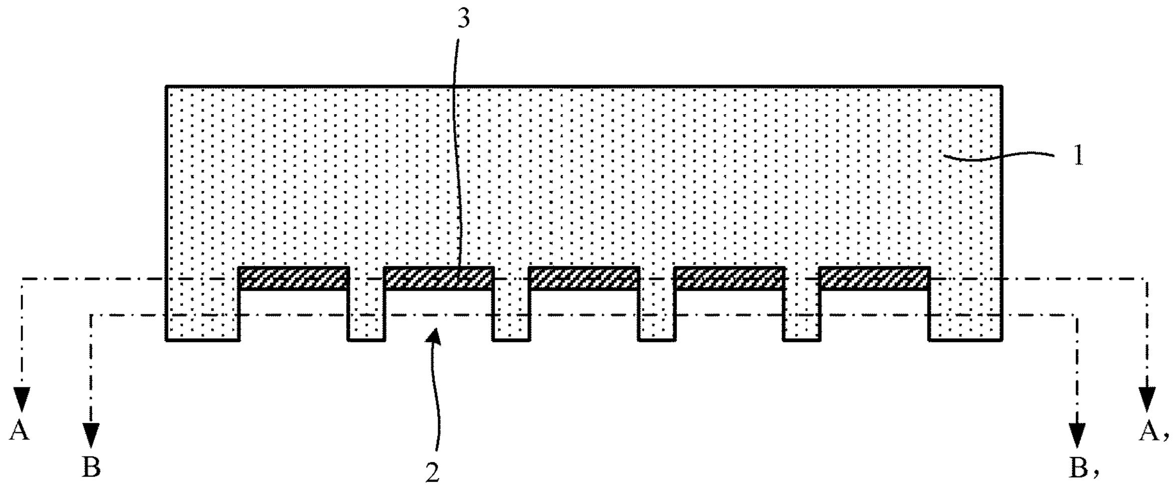
FIG. 2 shows a structural schematic diagram of the single-cell screening device of the present disclosure in a second section from the first surface toward the second surface.

In this embodiment, a single-cell screening device is provided. The single-cell screening device includes a body, and spray holes and a flow channel provided in the body. The body includes a first surface and a second surface arranged opposite to the first surface, see FIGS. 1-2. FIG. 1 shows a schematic diagram of the structure of the single-cell screening device in a first section from the first surface toward the second surface, and FIG. 2 shows a schematic diagram of the structure of the single-cell screening device in a second section from the first surface toward the second surface. The first section passes through the flow channel 4 and the spray holes 2, and the second profile does not pass through the flow channel 4.

Specifically, a plurality of spray holes are disposed in the body 1. The spray holes 2 extend from openings from the second surface, and extend toward the first surface without penetrating the first surface.

As an example, the spray holes 2 have a diameter less than twice the diameter of target single cells, to increase the probability of the target single cells' appearance.

Specifically, the spray holes 2 are provided with heating portions 3. The heating portions 3 are connected to top surfaces of the spray holes 2, for heating liquid entering the spray holes 2, so as to produce bubbles that will eject the cells entering the spray holes 2.

Specifically, the flow channel 4 extends from an opening on the first surface, and extends to the spray holes 2 in a predetermined path, to deliver a cell suspension into the spray holes 2.

As an example, as shown in FIG. 1, the flow channel 4 includes a main flow channel 4*a* and a plurality of sub-flow channels 4*b* connected to the main flow channel 4*a*, each of the spray holes 2 being connected to one of the sub-flow channels 4*b*.

As an example, the plurality of sub-flow channels 4*b* are distributed on two opposite sides of the main flow channel 4*a* as described in FIG. 1.

Figure 3:
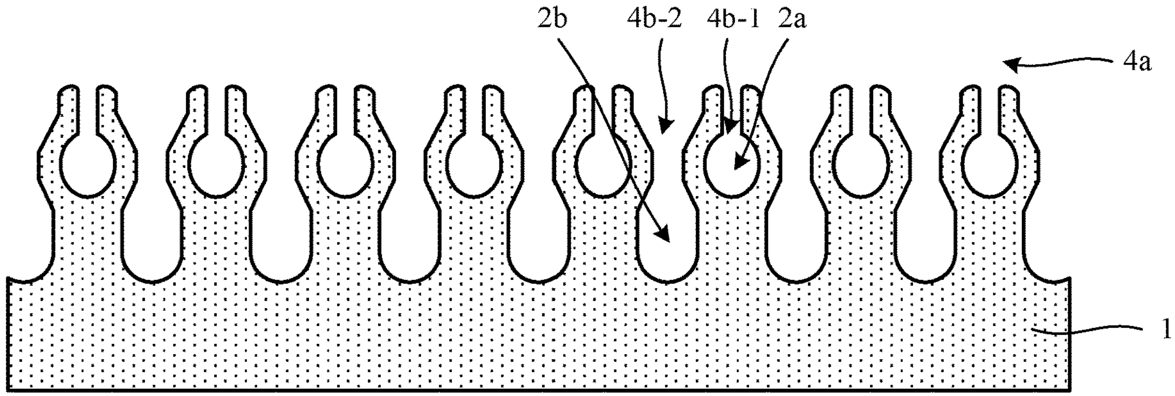
FIG. 3 shows a schematic diagram of a partial cross-section of the single-cell screening device of the present disclosure along the B-B' direction in FIG. 2.
Figure 4:
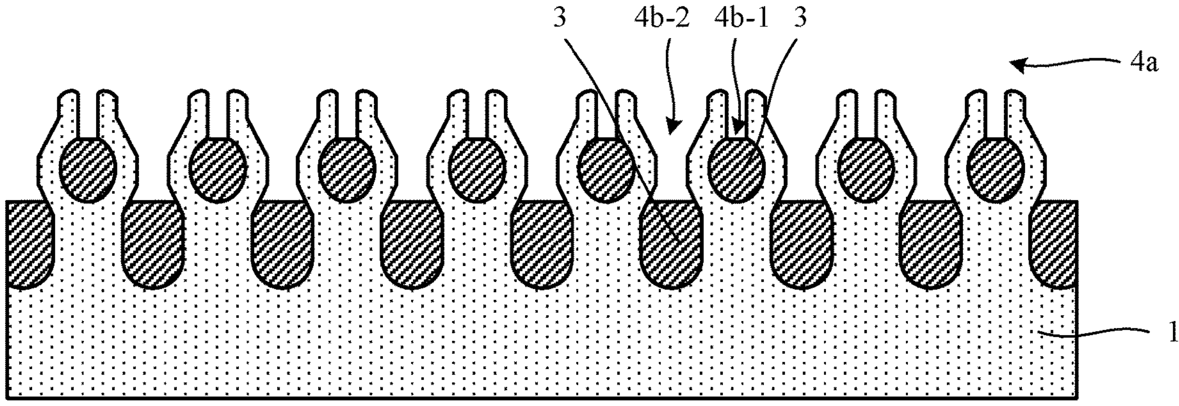
FIG. 4 shows a schematic diagram of a partial cross-section of the single-cell screening device of the present disclosure along the A-A' direction in FIG. 2.

Referring to FIGS. 3-4, FIG. 3 shows a schematic diagram of a partial cross-section of the single-cell screening device along the B-B' direction in FIG. 2, and FIG. 4 shows a schematic diagram of a partial section of the single-cell screening device along the A-A' direction in FIG. 2.

As an example, all the sub-flow channels 4*b* have the same length, or at least two of the sub-flow channels 4*b* have different lengths. In this embodiment, the flow channel 4 includes a first sub-flow channel 4*b*-1 and a second sub-flow channel 4*b*-2 respectively connected to one side of the main flow channel 4*a*. The second sub-flow channel 4*b*-2 has a length greater than the length of the first sub-flow channel 4*b*-1. The first sub-flow channel 4*b*-1 is connected to the first spray hole 2*a*, and the second sub-flow channel 4*b*-2 is connected to the second spray hole 2*b*. The design of the different lengths of the sub-flow channels allows for a denser arrangement of the spray holes and improves space utilization.

Figure 5:
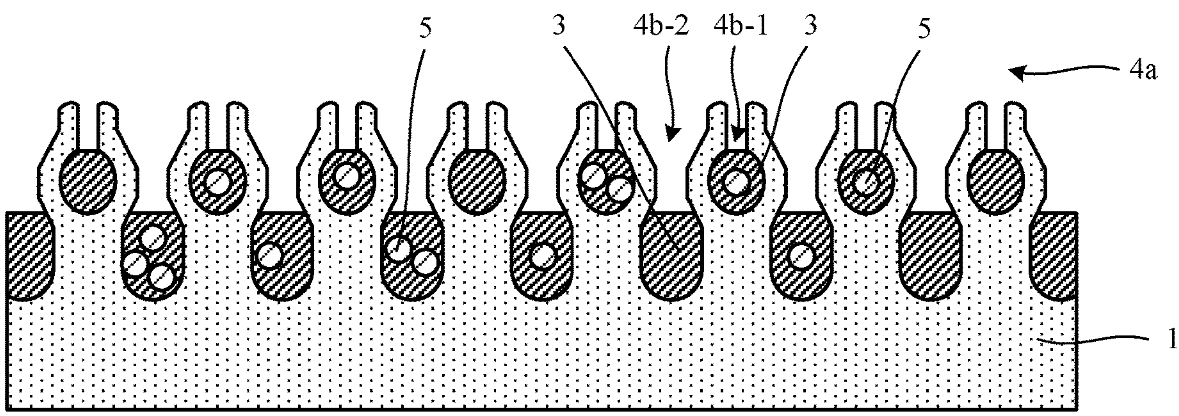
FIG. 5 is a schematic diagram showing the distribution of single cells, multiple cells and vacuoles in the single-cell screening device of the present disclosure.

FIG. 5 is a schematic diagram showing the distribution of single cells, multiple cells and vacuoles in the single-cell screening device. The cell suspension sequentially enters through the main flow channel 4*a* and the sub-flow channels 4*b* into the plurality of spray holes. Some of the spray holes contain a single cell 3, some of the spray holes contain a plurality of cells 3, and some of the spray holes contain only liquid but no cells, that is, vacuoles.

Figure 6:
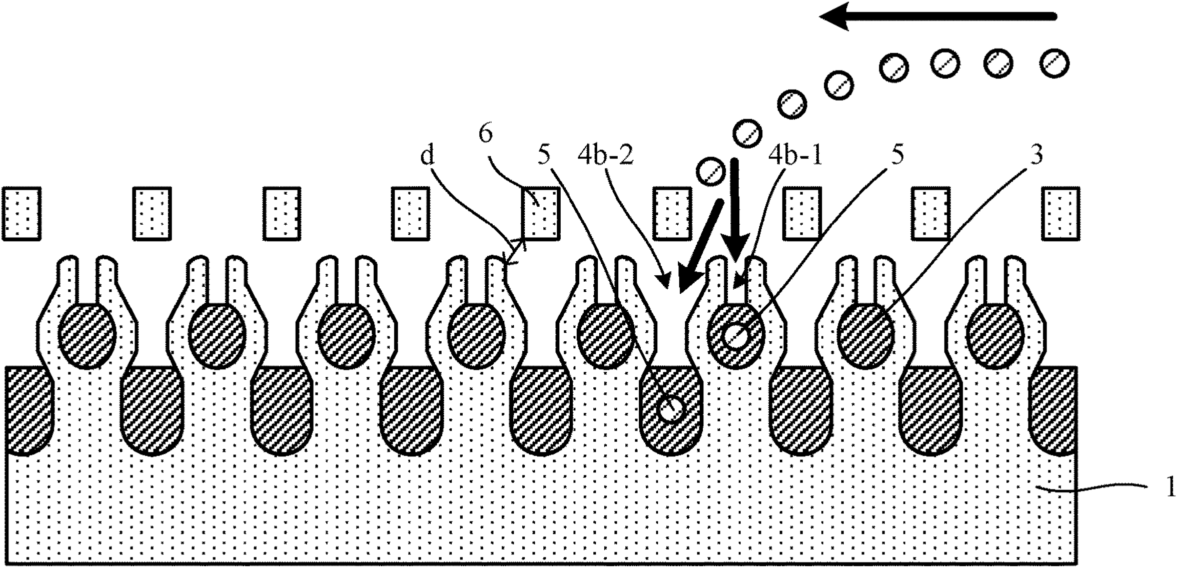
FIG. 6 is a schematic diagram showing the column array provided in the main flow channel for lining up the cells.

As an example, the main flow channel may further include a column array for lining up cells before the cell suspension enters the sub-flow channels, to increase the probability of a single cell appearing in a spray hole. FIG. 6 is a schematic diagram showing the column array provided in the main flow channel for lining up the cells.

As an example, the shortest distance d between each column 6 of the column array and a corresponding sub-flow channel closest to the column 6 is less than twice the diameter of the single cell to be screened.

The single-cell screening device of the present disclosure has a simple design and is easy to fabricate, which allows for rapid sorting of cells.

It is to be noted that the single-cell screening device may use a thermal bubble printing chip. The process of the heating portions 3 heating the liquid entering the spray holes 2 to produce bubbles for ejecting the cells entering the spray holes 2 may also be referred to as printing cells.

The single-cell screening device of the present disclosure may be a thermal Inkjet dispenser, which utilizes micro-heating portions in the micro-jet holes to heat the fluid surface, so that a tiny volume of fluid is instantaneously heated to vaporization, producing bubbles to propel the fluid or the substance in the fluid. Inkjet dispensers have the advantage of being fast and rapid, capable of printing over 1 million drops per second of tiny droplets around 20-60 microns in size, enabling single cell printing. The spray heads are also programmable, allowing for precise control of the printing process by a controller to produce products of better quality.

Embodiment 2

Figure 7:
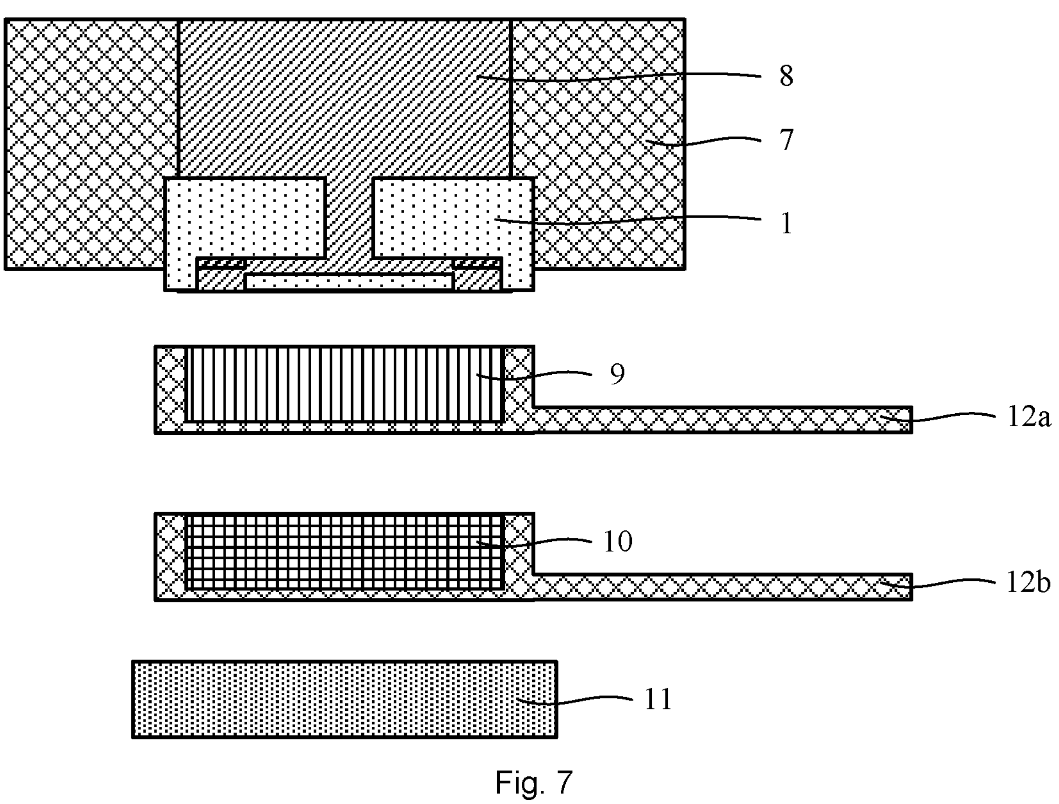
FIG. 7 is a schematic diagram showing the cross-sectional structure of the screening assembly of the present disclosure.

This embodiment provides a single-cell screening assembly including the single-cell screening device as described in embodiment 1. FIG. 7 is a schematic diagram showing the cross-sectional structure of the single-cell screening assembly. The assembly further includes a reservoir 7, a cell harvester 9, a waste liquid collector 10, and an optical system 11. The reservoir 7 is used to store a cell suspension 8. The reservoir 7 is provided with a liquid outlet for outputting the cell suspension 8 to a flow channel inside the body 1 of the single-cell screening device and further to the spray holes. The cell harvester 9 is located below the single-cell screening device for receiving target single cells ejected from the spray holes. The waste liquid collector 10 is located below the single-cell screening device for receiving non-target cells and liquid ejected from the spray holes. The optical system 11 is located below the single-cell screening device for identifying the location and the serial number of the spray holes containing the target single cells.

As an example, the cell harvester 9 moves by means of a mechanical arm 12*a*, and the waste liquid collector 10 moves by means of a mechanical arm 12*b*.

As an example, the optical system includes a bright field light source system for identifying the number and size of the cells. In this embodiment, the bright field light source system includes a microscope lens, a coaxial light path, a bright field light source, a condenser lens barrel, and a charge coupled device (CCD) camera, which are sequentially arranged according to a predetermined path.

As an example, the optical system includes a fluorescent light source system for identifying cells with specific antibody labeling. In this embodiment, the fluorescent light source system includes a microscope lens, a coaxial light path, a fluorescence filter, a fluorescent light source, a condenser lens barrel, and a CCD camera, which are sequentially arranged according to a predetermined path.

As an example, the cell harvester 9 includes a multi-well plate, such as a 96-well plate or a plate with another number of wells, each well 13 in the multi-well plate being used to receive preferably one target single cell.

Cell printing (spraying) using the single-cell screening assembly of this embodiment has a much higher cell printing speed than conventional methods, allowing for a rapid cell sorting process. The camera of the microscope of the optical system scans all samples in sequence and uses images to quickly identify locations of the target cells, and then the single-cell screening device sequentially performs the release of the target cells, while non-target cells can be released at the same time, thus greatly reducing the time of screening and sorting. The cell screening device of the present disclosure prints cells with minimal damage to the cells. The specific screening process can be found in embodiment 3.

Embodiment 3

This embodiment provides a single-cell screening method, which uses the single-cell screening assembly described in embodiment 2 for single-cell screening, including the operations of:

- S1: supplying, via the reservoir, a cell suspension to the single-cell screening device;
- S2: identifying, via the optical system, locations of spray holes containing the target single cells in the single-cell screening device;
- S3: moving the cell harvester to a predetermined position below the single-cell screening device, and driving, via a control circuit, the heating portions in the spray holes containing the target single cells, to sequentially eject single cells from the corresponding spray holes into the cell harvester;
- S4: moving the waste fluid collector to a predetermined position below the single-cell screening device, and driving, via a control circuit, the heating portions in the spray holes containing the non-target cells, to eject the contents in the corresponding spray holes into the waste fluid collector.

Figure 8:
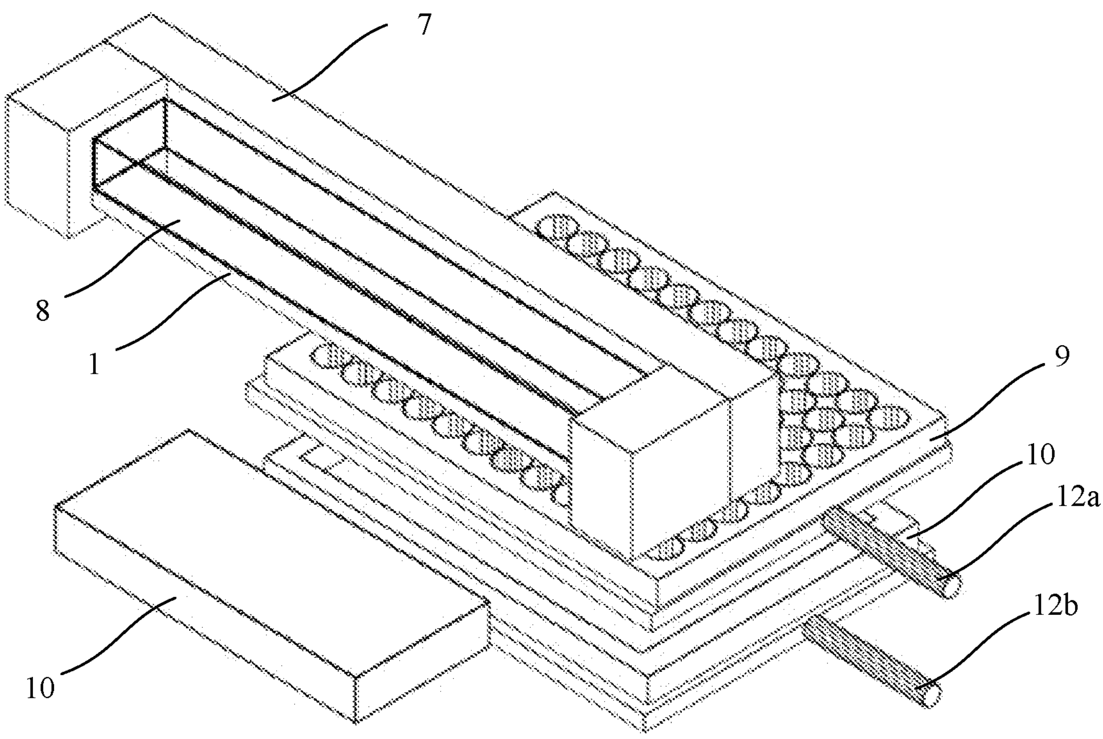
FIG. 8 is a schematic diagram showing the three-dimensional structure of the screening assembly of the present disclosure.

FIG. 8 shows a three-dimensional structure of the screening assembly. To better illustrate the body 1 of the single-cell screening device and the cell suspension 8, part of the side of the reservoir 7 is omitted from the illustration.

Figure 9:
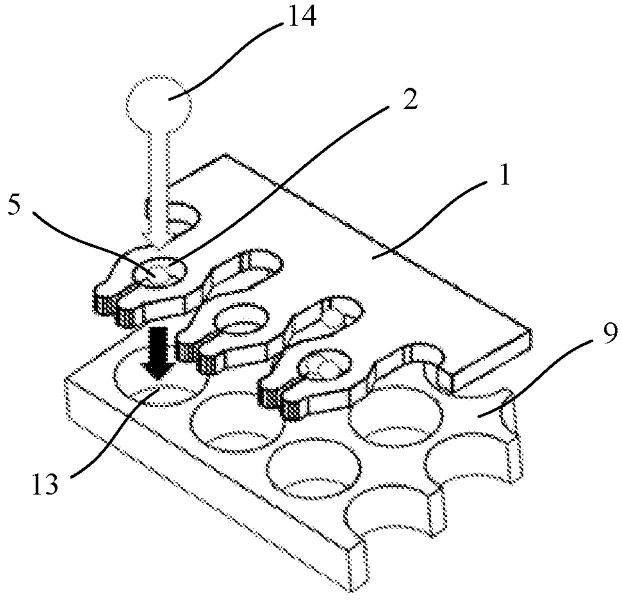
FIGS. 9-10 show schematic diagrams of the sequential ejection of the screened single cells into the wells of the single-cell harvester using the screening assembly of the present disclosure.
Figure 10:
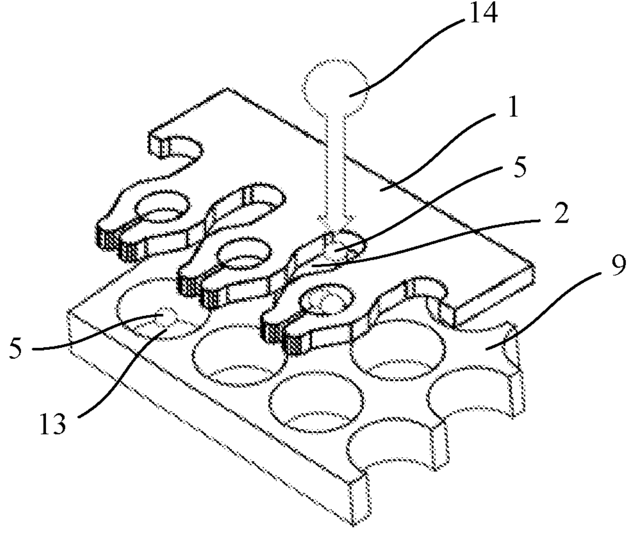

FIGS. 9-10 show schematic diagrams of the sequential ejection of the target single cells 5 into the wells 13 of the single-cell harvester 9 using the screening assembly, where the cells 5 are ejected by the bubbles 14 produced by liquid heated by the heating portions inside the spray holes.

As an example, after the cells are ejected, solution containing cells will be continuously supplemented into spray holes from which cells have just been released until none of the spray holes contains a target single cell.

Figure 11:
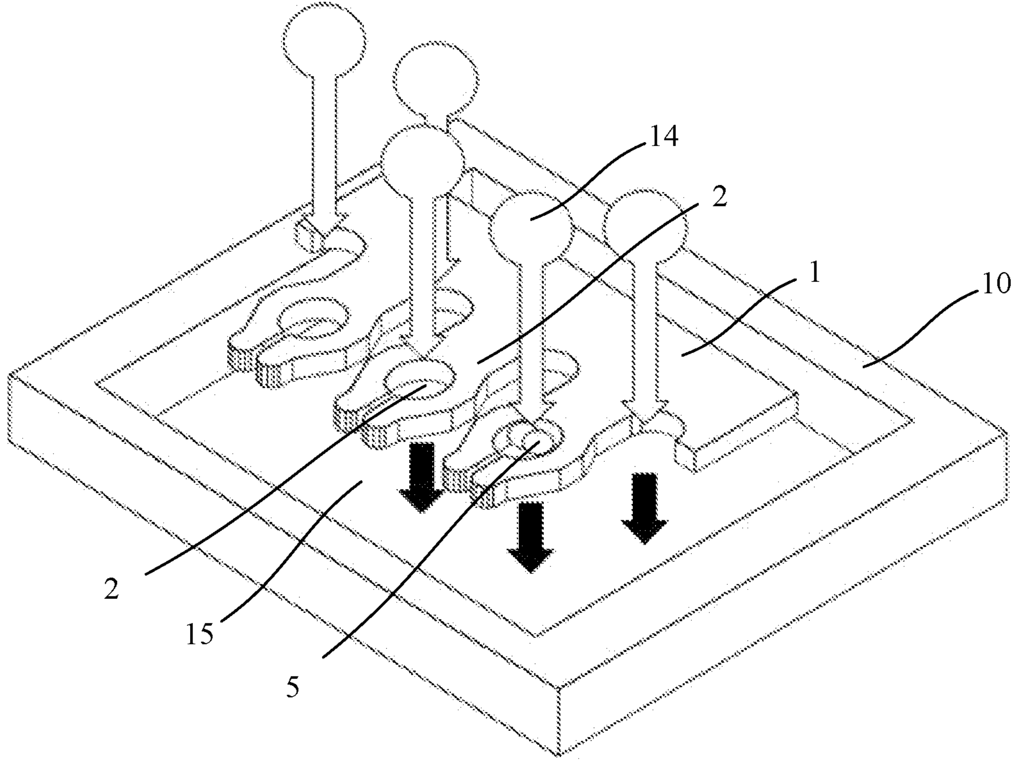
FIG. 11 shows a schematic diagram of using the screening assembly of the present disclosure to eject the contents of all the spray holes containing non-target cells into the waste liquid collector.

Referring to FIG. 11, at this time, the contents in all the spray holes containing non-target cells are ejected into a waste liquid collection tank 15 of the waste liquid collector 10.

After the waste liquid is collected, the waste liquid collector is moved sideways, by which time the sorting of target single cells and non-target cells (multiple cells, vacuoles) is completed. To continue sorting, repeat the above operations after replacing the cell harvester or waste liquid collector with a new one.

As an example, the cell harvester and the waste fluid collector are simultaneously moved below the single-cell screening device, and the waste fluid collector is located below the cell harvester. When all target single cells have been ejected, the cell harvester will be removed and the waste liquid collector will be raised to the previous position of the cell harvester.

As an example, the cell harvester moves by means of a mechanical arm 12*a*, and the waste liquid collector 10 moves by means of a mechanical arm 12*b*.

Cell printing (spraying) using the single-cell screening assembly of this embodiment has a much higher cell printing speed than conventional methods, allowing for a rapid cell sorting process. The camera of the microscope of the optical system scans all samples in sequence and uses images to quickly identify the location of the target cells, and then the single-cell screening device sequentially performs the release of the target cells, while non-target cells can be released at the same time, thus greatly reducing the time of screening and sorting. The cell screening device of the present disclosure prints cells with minimal damage to the cells.

The single-cell screening assembly of the present disclosure is suitable for sorting a variety of cells, including but not limited to circulating tumor cells (CTCs).

As an example, in this embodiment, CTC are sorted from a cell solution using a combination of fluorescent molecules and a bio-marker, spray holes containing single cells are detected after scanning all samples using an optical system, and then single cells are sequentially printed into a cell harvester using a single-cell screening device. After all the single-cell samples have been printed, the single-cell screening device is used to print everything in the non-target spray holes (including multiple cells and vacuolated droplets) into the waste liquid collector. After the sorting process is completed, the cell harvester contains only one single cell per well, and the waste liquid collector contains multiple cells and droplets.

Embodiment 4

The present disclosure provides a use of a single-cell screening device, including using the single-cell screening device described in embodiment 1 to eject cells, to create recoverable pores on surfaces of cell membranes, and using the pores for cell chromosome transfection.

It should be noted that the recovery of the pores on the cell membrane is a relatively random event, with the pores being able to exist for approximately 15 minutes in average, and cell chromosome transfection needs to occur before the recovery of the pores (that is, before the pores disappear).

In summary, the single-cell screening device of the present disclosure has a simple design and is easy to fabricate. Cell printing (spraying) using the screening assembly including the single-cell screening device has a much higher cell printing speed than conventional methods, allowing for a rapid cell sorting process. The camera of the microscope of the optical system scans all samples in sequence and uses images to quickly identify locations of the target cells. The target cells are sequentially released, while the non-target cells can also be released at the same time, thus greatly reducing the time of screening and sorting. The cell screening device of the present disclosure prints cells with minimal damage to the cells. The cell screening device of the present disclosure may have other applications, for example, the recoverable pores created on the surface of cell membrane during cell printing may be used as an application tool for cell chromosome transfection. Therefore, the present disclosure effectively overcomes various shortcomings in the existing technology and has high industrial utilization value.

The above-mentioned embodiments are merely illustrative of the principle and effects of the present disclosure instead of limiting the present disclosure. Modifications or variations of the above-described embodiments may be made by those skilled in the art without departing from the spirit and scope of the disclosure. Therefore, all equivalent modifications or changes made by those who have common knowledge in the art without departing from the spirit and technical concept disclosed by the present disclosure shall be still covered by the claims of the present disclosure.

What is claimed is:

1. A single-cell screening device, comprising:
a body, comprising a first surface, and a second surface arranged opposite to the first surface;
a plurality of spray holes, disposed in the body, wherein the spray holes extend from openings on the second surface and extend toward the first surface without penetrating the first surface;
heating portions, disposed in the spray holes and connected to top surfaces of the spray holes, the heating portions being used to heat liquid entering the spray holes to produce bubbles, wherein the bubbles eject cells entering the spray holes; and
a flow channel, disposed in the body, the flow channel extends from an opening from the first surface and extends to the spray holes according to a predetermined path, to deliver a cell suspension into the spray holes;
wherein the flow channel includes a main flow channel and a plurality of sub-flow channels connected to the main flow channel, each of the spray holes being connected to one of the sub-flow channels;
wherein the main flow channel includes a column array for lining up cells before the cell suspension enters the sub-flow channels.

2. The single-cell screening device according to claim 1, wherein the plurality of sub-flow channels are distributed on two opposite sides of the main flow channel.

3. The single-cell screening device according to claim 1, wherein the shortest distance between each column of the column array and a corresponding sub-flow channel closest to the column is less than twice a diameter of a single cell to be screened.

4. The single-cell screening device according to claim 1, wherein the spray holes have a diameter less than twice a diameter of target single cells.

5. A single-cell screening assembly, comprising the single-cell screening device according to claim 1, wherein the single-cell screening assembly further comprises:
a reservoir, used for storing the cell suspension, and is provided with a liquid outlet for outputting the cell suspension to the flow channel of the single-cell screening device;
a cell harvester, located below the single-cell screening device, for receiving target single cells ejected from the spray holes;
a waste liquid collector, located below the single-cell screening device, for receiving non-target cells and liquid ejected from the spray holes; and
an optical system, located below the single-cell screening device, for identifying locations and serial numbers of spray holes containing the target single cells.

6. The single-cell screening assembly according to claim 5, wherein the optical system comprises a bright field light source system for identifying the number and size of cells.

7. The single-cell screening assembly according to claim 6, wherein the bright field light source system comprises a microscope lens, a coaxial light path, a bright field light source, a condenser lens barrel, and a charge coupled device (CCD) camera, which are sequentially arranged according to a predetermined path.

8. The single-cell screening assembly according to claim 5, wherein the optical system comprises a fluorescent light source system for identifying cells with a specific antibody labeling.

9. The single-cell screening assembly according to claim 8, wherein the fluorescent light source system comprises a microscope lens, a coaxial light path, a fluorescence filter, a fluorescent light source, a condenser lens barrel, and a charge coupled device (CCD) camera, which are sequentially arranged according to a predetermined path.

10. The single-cell screening assembly according to claim 5, wherein the cell harvester comprises a multi-well plate, each well in the multi-well plate being used to receive one target single cell.

11. A single-cell screening method, comprising using the single-cell screening assembly according to claim 5 for single-cell screening, wherein the single-cell screening method comprises the following operations:
supplying, via the reservoir, a cell suspension to the single-cell screening device;
identifying, via the optical system, locations of spray holes containing the target single cells in the single-cell screening device;
moving the cell harvester to a predetermined position below the single-cell screening device, and driving, via a control circuit, the heating portions in the spray holes containing the target single cells, to sequentially eject single cells from the corresponding spray holes into the cell harvester; and
moving the waste fluid collector to a predetermined position below the single-cell screening device, and driving, via a control circuit, the heating portions in spray holes containing non-target cells, to eject contents in the corresponding spray holes into the waste fluid collector.

12. The single-cell screening method according to claim 11, wherein the contents in all the spray holes containing non-target cells are ejected into the waste liquid collector at the same time.

13. The single-cell screening method according to claim 11, wherein at this time, the cell harvester and the waste fluid collector are moved below the single-cell screening device, and the waste fluid collector is located below the cell harvester; when all the target single cells have been ejected, the cell harvester is removed and the waste liquid collector is raised to a previous position of the cell harvester.

14. The single-cell screening method according to claim 11, wherein the cell harvester and the waste liquid collector move by means of mechanical arms.

15. A method for creating recoverable pores on a surface of a cell membrane, comprising: ejecting cells using the single-cell screening device according to claim 1 to create the recoverable pores on the surface of the cell membrane, and performing cell chromosome transfection using the pores.

* * * * *